United States Patent [19]

Torres-Cardona et al.

[11] Patent Number: 5,959,138

[45] Date of Patent: Sep. 28, 1999

[54] SHORT CHAIN DIESTERS AND PROCESS FOR MAKING THE SAME

[75] Inventors: Mario-David Torres-Cardona, San Nicolás de los Garza; Jose-Odon Torres-Quiroga, San Pedro Garza García, both of Mexico

[73] Assignee: Industrial Organica S.A. DE C.V., Topo Chico, Monterrey, Mexico

[21] Appl. No.: 08/969,948

[22] Filed: Nov. 25, 1997

[51] Int. Cl.$^6$ .................................................. C07C 69/608
[52] U.S. Cl. ............................................................ 560/190
[58] Field of Search ............................................. 560/190

[56] References Cited

U.S. PATENT DOCUMENTS

| 4,105,855 | 8/1978 | Schulz et al. | 560/190 |
| 5,429,939 | 7/1995 | Misawa et al. | 435/67 |
| 5,523,494 | 6/1996 | Torres-Cardona et al. | 568/834 |

OTHER PUBLICATIONS

Handbook of Chemistry and Physics, The Chemical Rubber Publishing Co., pp. 774–775, Jan. 1961.

*Primary Examiner*—Johann Richter
*Assistant Examiner*—Dominic Keating
*Attorney, Agent, or Firm*—Abelman, Frayne & Schwab

[57] ABSTRACT

A process to obtain a product having a high content of zeaxanthin, lutein or mixtures thereof, as short chain organic acid diesters of zeaxanthin, lutein or mixtures thereof, that can be used mainly for the pigmentation of broilers and egg yolks, as well as an intermediate in the cantaxanthin(β,β-Carotene-4,4'-dione) and astaxanthin(3,3'-Dihidroxy β,β-carotene,4,4'-dione) synthesis, by reacting extracts obtained from marigold (Tagetes Erecta L.), or plant extracts that contain lutein, zeaxanthin or mixtures thereof in any proportion, with acetic or propionic anhydride under controlled conditions of temperature and pressure.

18 Claims, No Drawings

SHORT CHAIN DIESTERS AND PROCESS FOR MAKING THE SAME

BACKGROUND OF THE INVENTION

A. Field of the Invention

This invention is related to short chain diesters, and more particularly to a process for the obtention of a product with a high content of zeaxanthin, lutein or mixtures thereof, as short chain organic acid diesters of zeaxantine, lutein or mixtures thereof.

B. Description of the Related Art

The yellow carotenoids such as the lutein and the zeaxanthin, occur in marigold flowers as mono- or diesters, linked to long chain fatty acids such as palmitic, stearic or myristic acids, among others (Alam, A. U. (1968) *Lipids,* 3(2), 183; Gayle G. (1986) *J. Food Sci.,* 51(4), 1093).

It is assumed that in such chemical structure, the carotenoids are better protected against oxydative processes, so that the flower color is better preserved in nature.

However, in the pigmentation of broilers, it has been shown that the bioavailability of such carotenoid fatty esters is lower than when they are hydrolized, i.e. when they are fed as free carotenoids (Coon, C. N. (1976) *Poult. Sci.,* 551 841–847).

Applicant's have found that by saponification of the marigold carotenoids and their subsquent linking to short chain acids, such as formic, acetic or propionic, etc., an improvement in their bioavailability, and that a more stable form of the carotenoids is achieved.

The acetylation of carotenoids, zeaxanthin among others, has been carried out in laboratory scale since decades ago. The reported methodology specifically refers to a research, for elucidation purposes about the chemical structures of the carotenoids.

The carotenoid in pure form, zeaxanthin in this case, is dissolved in pyridine treating it with acetic anhydride and agitation at room temperature to obtain the acetylated derivative after several hours (Liaaen-Jensen, S. and Jensen, A. (1971) *Methods Enzymol.* 23, 586), or in a few minutes if the reactants mixture is maintained under reflux (Alam, 1968).

Another preferred chemical path to obtain the acetylated compound is to dissolve the zeaxanthin in pyridine and benzene to carry on the reaction at 20° C. with acetyl chloride, a few minutes later (Bartlett, L. (1969) *J. Chem. Soc.* C, 2538).

In the process acording with the present invention, marigold extracts containing saponified and isomerized carotenoids (Torres, et al. 5,523,494 6/1996, 568/834), are treated directly with acetic anhydride, or propionic anhydride in such a way as to obtain the short chain organic acid diester derivatives of the zeaxanthin, lutein or mixtures thereof, present in such extracts.

SUMMARY OF THE INVENTION

It is a further a main objective of the present invention to provide a product having a high content of zeaxanthin, lutein or mixtures thereof, in the form of short chain organic acid diesters of zeaxanthin, lutein or mixtures thereof, which can be used mainly in the pigmentation of broilers skin and egg yolks.

It is a further main objective of the present invention to provide a process for the obtention of a product with a high content of zeaxanthin, lutein or mixtures thereof, in the form of short chain organic acid diesters of zeaxanthin, lutein or mixtures thereof, which can be used mainly in the pigmentation of broilers skin and egg yolks.

It is also a main objective of the present invention to provide a process of the above disclosed nature, by reacting short chain organic anhydrides to saponified extracts containing carotenoids, in an inert atmosphere of carbon dioxide, nitrogen or a mixture of both under controlled conditions of temperature and pressure.

It is another main objective of the present invention to provide a process of the above disclosed nature in which saponified extracts containing carotenoids are treated without the need of any solvent at all.

It is still another main objective of the present invention, to provide a process of the above disclosed nature, wherein the product or its formulations can be used for the pigmentation of broiler skin and egg yolk or as a pigmenting agent in aquaculture.

It is an additional object of the present invention to provide a process of the above disclosed nature wherein the zeaxanthin diester obtained can be used as an intermediate in the synthesis of astaxanthin or cantaxanthin, for the obtention of such short chain diesters of zeaxanthin, lutein or mixtures thereof.

These and other objectives and advantages of the present invention will be apparent to those persons having ordinary skill in the art, from the following detailed description of the invention.

DETAILED DESCRIPTION OF THE INVENTION

The chemical process is carried out according to the following reaction:

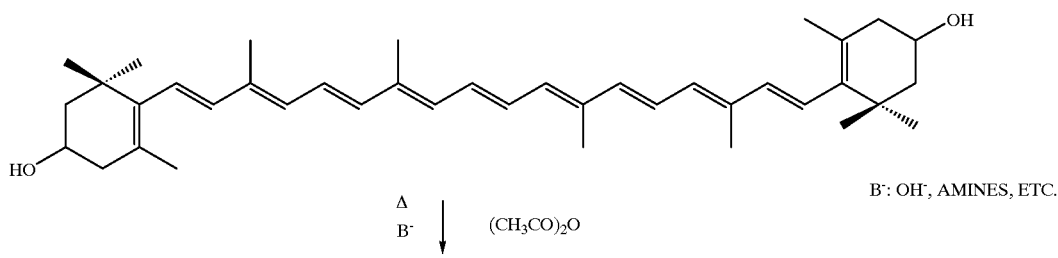

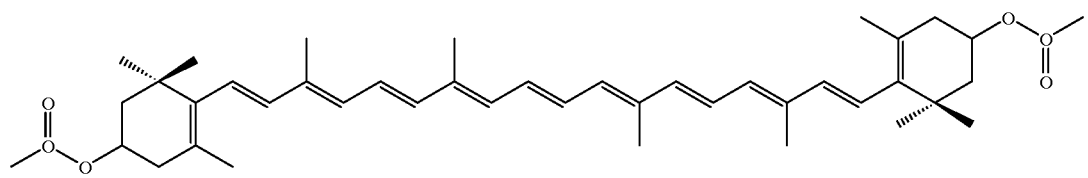

ZEAXANTHINE DIACETATE

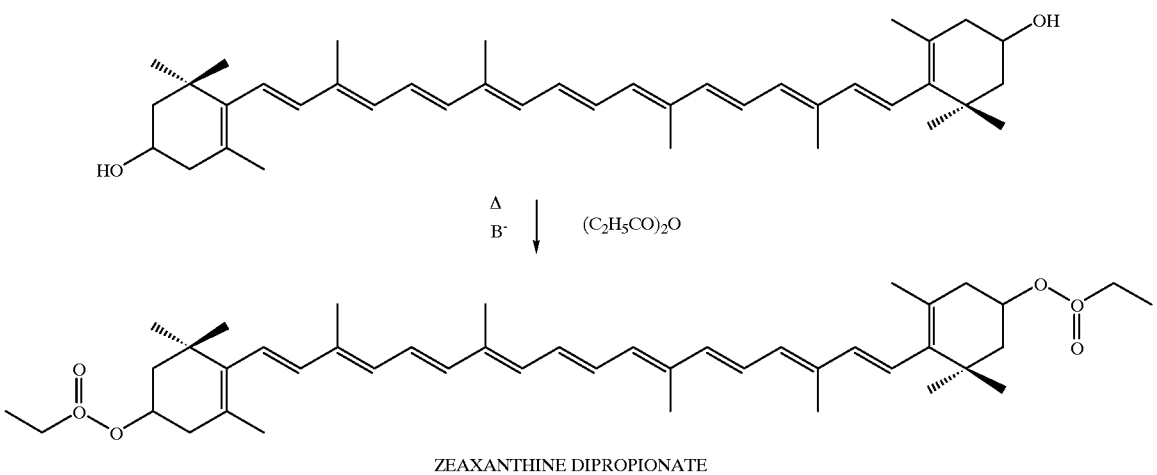

ZEAXANTHINE DIPROPIONATE

The saponified marigold extract containing the zeaxanthin, has been obtained according to the procedure reported by Torres, et al. (1996), but any pigmenting formulation or extract containing zeaxanthin can be used. Regardless of the raw material employed, it should preferably be moisture free before acetylating with acetic anhydride, or before treatment with propionic anhydride.

The carotenoid containing substrate is maintained at a temperature in the range of 25° C. to 140° C., but preferably between 40° C. and 100° C.

When a crude marigold extract containing the saponified and isomerized carotenoids, enters into the reaction with the acetic or propionic anhydride, its residual fatty acids and other lipids present occur as the sodium or potassium salts.

Acetylation Reaction

The acetic anhydride is slowly added to the extract in a reaction vessel under agitation, in a proportion from 0.2 to 2.0 parts by weight for one part of the pigmenting concentrate, which is in the form of a sodium or potassium soap (a heavy paste highly soluble in water). The reaction mixture is partially soluble in the acetic anhydride. However, as the acetylation reaction advances, an oily phase separates from the reaction media, mainly composed of acetic acid and sodium or potassium acetates in aqueous solution, from which it easily separated by decanting. The acetylation vessel wherein the reaction takes place should be kept under an inert atmosphere, in order to avoid the intensive degradation of the xanthophylls. An inert diluent such as ethylene glycol or propylene glycol or an aliphatic or cyclic hydrocarbon can be used to reduce the viscosity of the mixture.

The reaction time depends on the temperature and can be from 6 minutes to 24 hours, but preferably from 4 to 18 hours.

| Parameter | Trial 1 | Trial 2 | Trial 3 | Trial 4 |
|---|---|---|---|---|
| Acetic anhydride: extract Ratio | 0.5 | 2.5 | 1.0 | 2.0 |
| Reaction time, hrs. | 16 | 16 | 20 | 12 |
| Reaction temperature, °C. | 90 | 80 | 100 | 60 |
| Pressure, mm Hg | 750 | 760 | 750 | 760 |
| Mono-hydroxycarotenoids % | 4.2 | 1.5 | 1.7 | 2.8 |
| Di-hydroxycarotenoids % | 2.1 | 1.3 | 1.3 | 0.8 |
| Aceto-carotenoids % | 88.5 | 91.8 | 89.6 | 90.2 |

Propionation Reaction

Propionic anhydride is slowly added to the extract in a reaction vessel under agitation, in a proportion from 0.2 to 3.0 parts by weight to one part of the pigmenting concentrate, which is in the form of sodium or potassium soap (a heavy paste highly soluble in water). The reaction mix is partially soluble in the propionic anhydride. However as the propionation reaction advances, an oily phase separates from the reaction media, mainly composed of propionic acid and sodium or potassium propionates in aqueous solution, from which it is easily separated by decanting. The reaction vessel should be kept under an inert atmosphere to avoid degradation.

The reaction time depends on the temperature and can be from 5 minutes to 24 hours, but preferably from 3 to 17 hours.

| Parameter | Trial 1 | Trial 2 | Trial 3 | Trial 4 |
|---|---|---|---|---|
| Propionic Anhdride:extract Ratio | 0.8 | 2.5 | 2.0 | 3.0 |
| Reaction time, hrs | 6 | 4 | 4 | 3 |
| Reaction temperature, °C. | 70 | 60 | 80 | 80 |
| Pressure, mm Hg. | 760 | 780 | 760 | 780 |
| Mono-hydroxycarotenoids % | 4.1 | 1.5 | 1.8 | 0.7 |
| Di-hydroxycarotenoids % | 2.3 | 1.0 | 0.6 | 1.0 |
| Propionate-carotenoids | 86.0 | 90.0 | 89.0 | 91.0 |

The saponified extracts used as the raw material in the above described process, contain approximately 92% of di-hydroxy carotenoids, and 1–2% of mono-hydroxy carotenoids, quantified according to the AOAC method.

The identification and quantification of the pigments involved was carried out following the HPLC techniques mentioned by Torres, et al.( 1996), as well as by the use of other spectroscopic techniques as IR, UV, $^1$HNMR, etc., widely used in carotenoids identification.

The end product can be formulated as an aqueous emulsion, or it can be dispersed by means of a carrier to obtain pre-mixtures of a given concentration of zeaxanthin, lutein or mixtures thereof in the form of short chain organic acid diesters, to be used as a pigmenting agent for broiler's skin, egg yolks, or shrimps and salmon in aquaculture.

We claim:

1. A process for obtaining short chain organic acid diesters of mono- or polyhydroxylated carotenoids, from saponified extracts containing carotenoids, comprising:

reacting 0.2 to 3.5 parts of acetic or propionic anhydride, slowly under agitation, with one part of said saponified extracts containing carotenoids saponified with sodium or potassium hydroxide, in the absence of solvents, the process proceeding with the formation of a member selected from the sroup consisting of acetic acid and sodium acetate acetic acid and potassium acetate, propionic acid and sodium propionate, or propionic acid and potassium propionate.

2. The process as claimed in claim 1, wherein the carotenoids are selected from the group consisting of yellow carotenoids, lutein or zeaxanthin.

3. The process as claimed in claim 1, wherein saponified extracts containing carotenoids are obtained from extracts of marigold flowers, marigold meal, yellow corn, yellow corn gluten, or alfalfa.

4. The process as claimed in claim 2, wherein the zeaxanthin is in its free hydrolyzed form.

5. The process as claimed in claim 1, wherein the lutein or any other hydroxycarotenoid or mixtures thereof are hydrolized.

6. The process as claimed in claim 1, wherein the proportion of acetic anhydride is from 0.2 to 2.0 parts by weight, for one part of extract.

7. The process as claimed in claim 1, wherein the proportion of propionic anhydride is from 0.5 to 3.5 parts by weight for one part by weight of extract.

8. The process as claimed in claim 1, wherein the saponified extract is moisture free.

9. The process as claimed in claim 1, wherein the saponified extract is obtained from an alkaline reaction, containing residual NaOH, KOH or a mixture of both, or any other alkaline or alkaline-earth metal hydroxides, as well as organic bases selected from the group consisting of morpholine, ethylamine, diethylamine and ethanolamine.

10. The process as claimed in claim 1, wherein the reaction time is from 5 minutes to 12 hours.

11. The process as claimed in claim 1, wherein the reaction temperature is from 25° C. to 140° C.

12. The process as claimed in claim 1, wherein the reaction is carried out in an inert atmosphere of carbon dioxide, nitrogen, or a mixture of both.

13. The process as claimed in claim 1, wherein the reaction product contains from 5% to 90% of zeaxanthin diacetate.

14. The process as claimed in claim 1, wherein the reaction product contains from 5% to 90% of zeaxanthin di-propionate.

15. The process as claimed in claim 6 wherein the proportion of acetic anhydride is from 0.5 to 1.5 parts by weight, for one part of extract.

16. The procss as claimed in claim 7, wherein the proportion of propionic anhydride is from 0.5 to 1.5 parts by weight for one part by weight of extract.

17. The process as claimed in claim 1, wherein the reaction time is from about 2 to about 10 hours.

18. The process as claimed in claim 1, wherein the reaction temperature is from about 40° C. to about 100° C.

* * * * *

UNITED STATES PATENT AND TRADEMARK OFFICE
CERTIFICATE OF CORRECTION

PATENT NO. : 5,959,138
DATED : September 28, 1999
INVENTOR(S) : Torres-Cardona et al.

It is certified that error appears in the above-identified patent and that said Letters Patent is hereby corrected as shown below:

Columns 3 and 4, in the structural formula for zeaxanthine diacetate, at the right end terminal portion thereof, delete 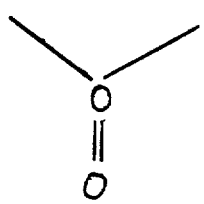 insert -- 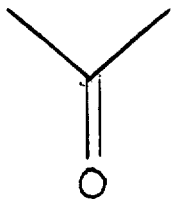 --.

Columns 3 and 4, in the structural formula for zeaxanthine dipropionate, at the right end terminal portion thereof,

UNITED STATES PATENT AND TRADEMARK OFFICE
CERTIFICATE OF CORRECTION

PATENT NO. : 5,959,138
DATED : September 28, 1999
INVENTOR(S) : Torres-Cardona et al It is certified that error appears in the above-identified patent and that said Letters Patent is hereby corrected as shown below:

Claim 1, line 9 thereof, delete "sroup", insert --group--.
line 10, between "sodium acetate" and "acetic acid"
insert a --,--.

Signed and Sealed this

Seventh Day of November, 2000

Attest:

Q. TODD DICKINSON

Attesting Officer    Director of Patents and Trademarks